United States Patent [19]
Page, Jr. et al.

[11] 3,942,392
[45] Mar. 9, 1976

[54] DENTAL HANDPIECE
[75] Inventors: Joe W. Page, Jr., Santa Ana; Paul H. Stahlhuth, Mission Viejo, both of Calif.
[73] Assignee: Joe W. Page, Jr., Huntington Beach, Calif.
[22] Filed: June 10, 1974
[21] Appl. No.: 477,803

[52] U.S. Cl. ............................ 74/750 R; 415/503
[51] Int. Cl.² .................................... F16H 3/44
[58] Field of Search ............... 74/750 R; 415/503; 418/266, 270

[56] References Cited
UNITED STATES PATENTS
| | | | |
|---|---|---|---|
| 3,430,521 | 3/1969 | Kulman | 74/750 R |
| 3,439,422 | 4/1969 | Doeden et al. | 415/503 X |
| 3,832,088 | 8/1974 | Cromie | 415/503 X |

Primary Examiner—Samuel Scott
Assistant Examiner—Frank H. McKenzie, Jr.
Attorney, Agent, or Firm—Fred N. Schwend

[57] ABSTRACT

A straight dental handpiece comprising a pair of telescoping housing barrels which can swivel relative each other, one containing a chuck and the other containing a vane type air motor. A change speed transmission is entrained between the motor and the chuck, such transmission being adjustable to change speeds by relative endwise movement of the barrels. Opening and closing of the chuck is accomplished by relative rotation thereof a limited amount. A reversing valve, also on the handpiece, is movable into either of two positions to apply air under pressure to either of two passages to drive the motor in one direction or the other.

9 Claims, 10 Drawing Figures

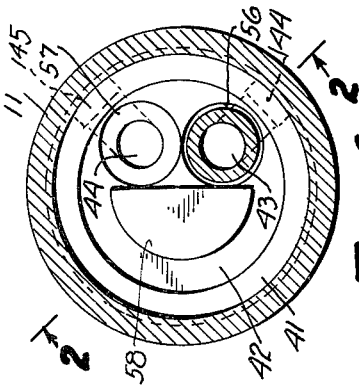
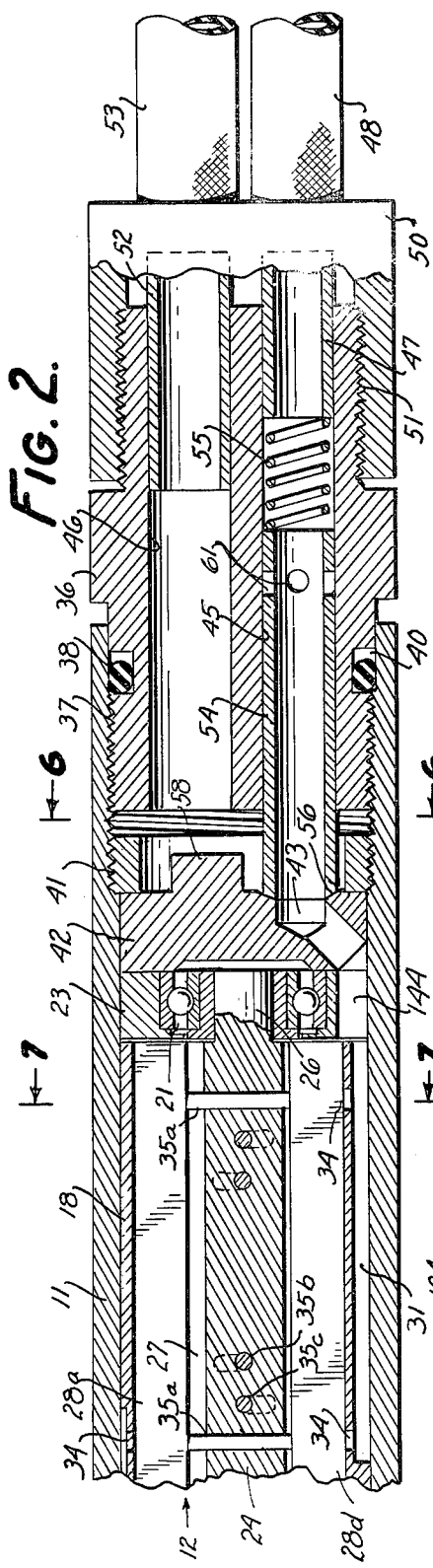
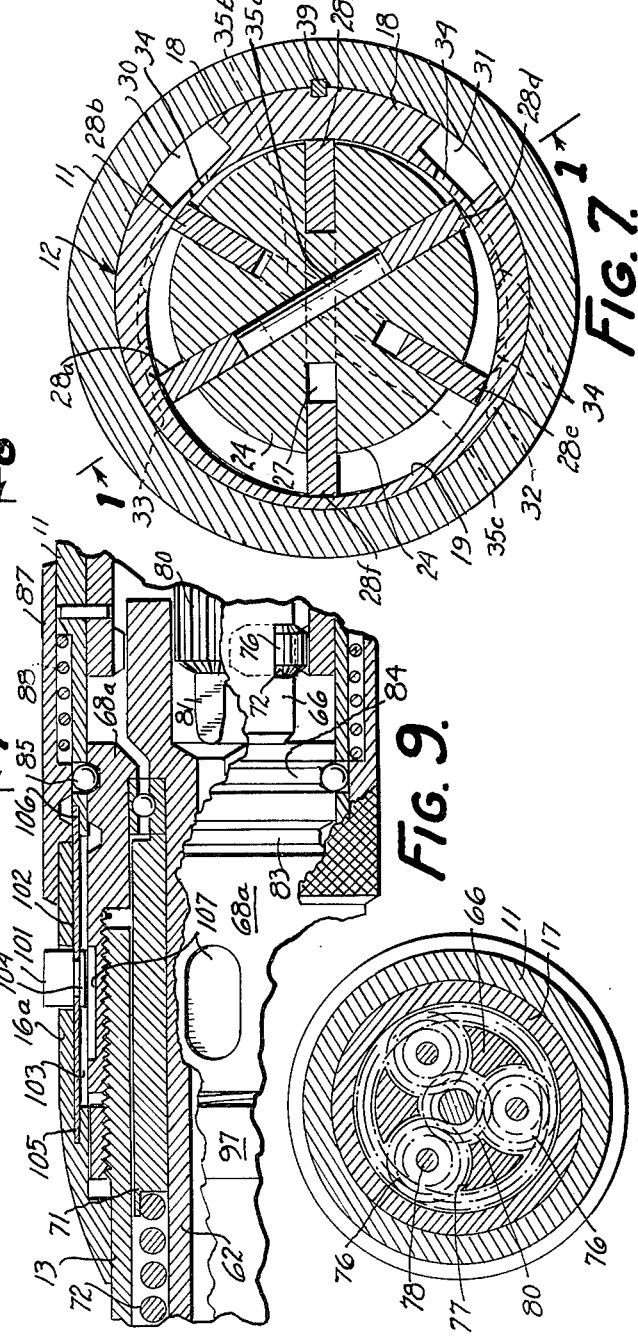
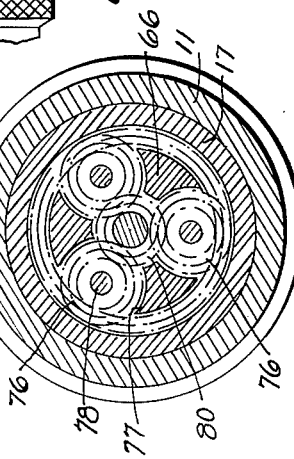

3,942,392

DENTAL HANDPIECE

BACKGROUND OF THE INVENTION

1. Field Of The Invention

This invention relates to fluid driven dental handpieces, particularly of the straight type.

2. Description Of The Prior Art

Modern dental handpieces of the above type generally comprise a chuck or collet which is powered by an air driven motor located in the handpiece itself. Turbine motors are not generally satisfactory for straight type handpieces as they operate most efficiently at high speeds, on the order of 250,000 rpm or more, and have relatively low torque. The speed of the turbine can be reduced by throttling the supply of air applied thereto under pressure but in doing so, the torque is further reduced.

For certain types of dental work, it is often desirable to operate a handpiece at relatively lower speeds and at higher torque. For example, it has been found that certain tooth cleaning, drilling and other operations are best performed at speeds on the order of 5,000 rpm whereas certain polishing operations are better performed at somewhat higher speeds, on the order of 15,000 to 25,000 rpm. Vane type air driven motors with gear reduction have been used heretofore in order to obtain such lower speeds and higher torque. However, here also, reduction in speed, as required for certain types of dental operations, is generally accomplished by throttling the air supply which tends to reduce the torque of the motor. Further, the vanes in such vane type motors tend to stick in retracted positions in their rotor slots due to accumulation of foreign matter therein. Such foreign matter is partly derived from products of internal motor wear. Such sticking results in erratic motor start-up, requires excessive air pressure and generates unpredictable break-away speeds.

Accordingly, a principal object of the present invention is to provide a compact dental handpiece or the like including an air motor and a readily adjustable change speed transmission means intermediate the motor and the chuck.

Another object is to facilitate selection of different drive ratios in a speed transmission means in a dental handpiece or the like.

Another object is to provide a simple and compact chuck for a dental handpiece or the like which is readily adjustable between open and closed conditions.

Another object is to reduce sticking of vanes in retracted positions in the slots of a vane type air motor for dental handpieces or the like.

Another object is to enable a swivel action between the finger grip area of a forward barrel and a rear barrel to nulify a build-up of torsional forces in the flexible conduits between the handpiece and the source of air under pressure.

Another object is to eliminate the need for periodic lubrication of the operating parts.

Another object is to facilitate dismantling of a dental handpiece of the above type.

STATEMENT OF THE INVENTION

According to the present invention, a dental handpiece is provided comprising a rotatable collet or chuck driven by an air motor through a change speed transmission, all mounted within the housing of the handpiece. In one aspect of the invention, the housing is in the form of a pair of telescoping barrels and the speed of the transmission is changed by relative positioning of the barrels. Opening and closing of the chuck is also accomplished by relative movement of the barrels. A reversing valve is provided which is rotatably mounted on the handpiece to apply air under pressure to either of two passages for driving the motor in either of opposite directions. The air motor is of the vane type with means for positively precluding diametrically opposed vanes from sticking in their slots in retracted positions. A part of the reversing valve may be displaced by a suitable tool to permit removal of the valve and dismantling of the handpiece.

BRIEF DESCRIPTION OF THE DRAWINGS

FIGS. 1 and 2 jointly form a longitudinal sectional view through a straight dental handpiece embodying the present invention and illustrate the same in a slow speed setting.

FIG. 6 is a transverse sectional view taken along the line 6—6 of FIG. 2, illustrating part of the reversing controls for the air motor.

FIG. 7 is a transverse sectional view taken along the line 7—7 of FIG. 2, illustrating the air motor.

FIG. 8 is a transverse sectional view taken along the line 8—8 of FIG. 1, illustrating the planetary gear drive system.

FIG. 9 is a fragmentary longitudinal sectional view illustrating an alternate means for locking the forward housing for opening or closing the collet.

DESCRIPTION OF THE EMBODIMENT SHOWN IN FIGS. 1 TO 8

Figure 1:
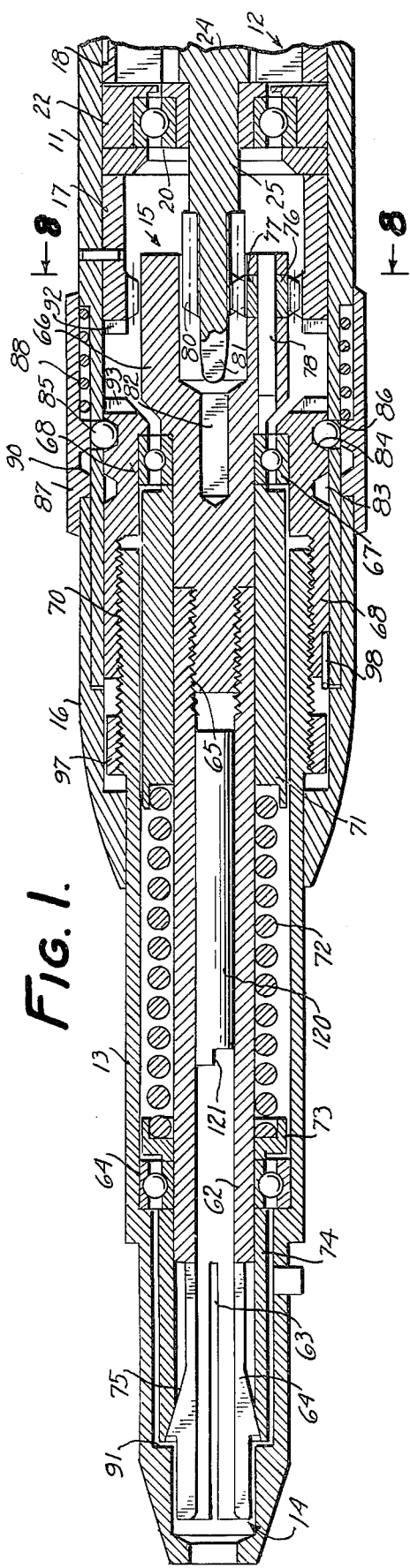

In general, the handpiece comprises a rear outer housing barrel 11 containing an air motor generally indicated at 12, and a forward inner housing barrel 13 slideable and rotatable within the outer barrel 11 and containing a collet or chuck generally indicated at 14 for a dental burr or other dental tool. A change speed transmission generally indicated at 15 is provided intermediate the motor 12 and collet 14 to enable the speed of the collet drive to be changed from a high speed 1 to 1 ratio, i.e., a direct drive to a low speed 1 to 4 ratio.

More specifically, the rear barrel 11 has integrally secured thereto by a suitable adhesive a counter-bored nosepiece 16. A ring gear 17, forming part of the transmission unit 15, is also suitably secured within the barrel 11.

An air motor cylinder or stator 18, FIGS. 1, 2 and 7, is also suitably secured within the barrel 11 and is located between two ball bearings 20 and 21 which are fitted within bearing housings 22 and 23, respectively, suitably secured within the barrel 11. The cylinder 18 has a bore 19, FIG. 7, therein whose axis is eccentric to the axis of the barrel 11 and bearings 20 and 21.

A rotor 24 is located within the bore 23 and has trunnion bearing portions 25 and 26 supported for rotation within the bearings 20 and 21 respectively. The outer periphery of the rotor 24 is concentric with the axes of the bearings 20 and 21 and six equally-angularly spaced radially extending slots 27 are formed along the length thereof to receive mating 28a 28a to 28f adapted to slide radially within the slots.

In order to convey air to and from the motor 12 to drive the same in either direction, two longitudinally extending passages 30 and 31 are formed along the length of the cylinder 18 and are located 90° apart, as viewed in FIG. 7. Parts of such passages also extend circumferentially approximately 60° as indicated at 32 and 33, and small holes 34 are formed in the wall of cylinder 18 intermediate the passages 32, 33 and the bore 19 of the cylinder to convey air under pressure to one side of the rotor 24 and to exhaust the air from the other side of the rotor during driving movement of the latter in either direction.

According to one aspect of the invention, and in order to substantially eliminate sticking of the vanes 28a, etc., in the rotor slots 27 of the rotor 24 which would otherwise eliminate or reduce the available starting torque, the pairs of diametrically opposed vanes are held to a minimum total diametrical dimension by pairs of spaced pins 35a, 35b, and 35c slideably mounted within bearing holes formed radially through the rotor 24. For example, vanes 28a and 28d are separated by pins 35a while vanes 28b and 28e are separated by pins 35b, which are spaced axially from the pins 35a, and pins 35c separate vanes 28c and 28f. Thus, the diametrically opposed vanes of each pair slide in unison radially of the rotor during rotation of the latter. Such pins 35a, etc., maintain a close running clearance between the vanes 28a to 28f and the rotor bore 19.

In order to introduce air under pressure to either of the passages 30 and 31 to determine the direction of rotation of the rotor 24, and to exhaust such air through the other passage, a reversing control valve 36 is screw-threaded at 37 within the rear end of the barrel 11 for limited rotation. An 0-ring 38 of an elastomeric material is located within a groove 40 in the valve 36 and slideably engages the inner surface of the barrel 11 to prevent leakage of air along the threads 37.

Also threaded in the threads 37 is an annular motor retaining nut 41 which maintains a valve plate 42 in intimate contact with the bearing housing 23, a longitudinal key 39 being provided to prevent rotation of the valve plate 42, the bearing housings 22 and 23, the cylinder 18 and the ring gear 17 relative to the barrel 11.

A pair of openings 43 and 44, see also FIG. 6, are formed in the valve plate 42 and these communicate through respective slots 144 and 145 in the bearing housing 23 with respective ones of the passages 31 and 30 in cylinder 18.

The reversing valve 36 is provided with an air inlet passage 45 and an air exhaust passage 46 extending longitudinally through. A tube 47 suitably affixed in the passage 45 communicates with a flexible air inlet conduit 48 carried by a cap member 50 threadably secured to the reversing valve 36 at 51. Likewise, a tube 52 secured in the exhaust passage 46 communicates with a flexible exhaust conduit 53 also carried by the cap member 50.

The inlet conduit 48 leads to a suitable air pump, or other supply of air under pressure while the exhaust conduit 53 leads to a suitable sound muffling device preferably located remotely from the handpiece so that any noise generated or conducted by the air passing through the air motor 12 will not disturb either the dentist or the patient.

An air inlet tube 54 slideably mounted within the passage 45 is closely fitted to minimize air leakage. The tube 54 is yieldably urged forward by a compression spring 55 extending between the same and tube 47 to maintain a frusto-conical forward end thereof in intimate sealing contact with a mating annular chamfered section 56 formed in the valve plate 42 surrounding the passage 43. A similar chamfered section 57, FIG. 6, is formed in the plate 42 surrounding the passage 44. The outlet passage 46 merely communicates with the space intermediate the valve 36 and the plate 42.

By rotating the valve 36 through 90°, the inlet tube 54 may be connected to the passage 44, and in either position, engagement of the tube 54 with the chamfered surface 56 or 57 will act to seal the connection and to detent the ring in either of such two positions.

From the foregoing it will be seen that when the valve 36 is set in its illustrated position air under pressure is transmitted through tube 54, passages 43, 144, 31 and holes 34 to exert pressure against the adjacent two or three vanes, causing a clockwise rotation of the rotor 24, as viewed in FIG. 7. Exhaust air is carried around the periphery of the rotor by the vanes and is exhausted through the holes 34 in the opposite passage 30 from whence it is conveyed through passages 145, 44 and exhausted through passage 46 and conduit 53. By rotating valve 36 through 90°, the inlet tube 54 will be aligned with passage 145 in the valve plate 42, causing rotation of the rotor 24 in a counterclockwise direction, in which case the exhausted air will pass through passage 31 to the exhaust passage 46.

A raised semi-circular boss 58 or other stop means is formed on the valve plate 42 to limit rotation of the reversing valve 36 through substantially 90° and to prevent accidental or intentional unscrewing of the reversing valve 36. However, when it is desired to remove the reversing valve 36 for access to the interior of the handpiece, the cap 50 is removed and a suitable hook (not shown) is passed through the tubes 47 and 54 to catch within one of several holes 61 formed in the latter. The tube 54 is then withdrawn beyond the level of the boss or stop 58, whereupon the valve 36 may be completely unscrewed from the barrel 11.

In case it is desired to permit the exhaust air to escape at the handpiece, the conduit 53 may be removed and air exhaust openings could be formed in the valve member 36 leading from the exhaust passage 46 to the atmosphere.

Describing now the collet and the change speed transmission, the collet 14 is formed on the forward end of a collet tube 62 which is slotted as shown at 63 to form four radially flexible collet fingers 64 effective to grip a suitable dental burr or other tool, not shown. The tube 62 is slideably mounted within the inner race of a ball bearing 64 fitted within the forward barrel 13 and is attached by screw-thread 65 to a planetary gear carrier 66 forming part of the drive transmission unit 15 and mounted within a ball bearing 67 fitted within a shift ring member 68 which is screw-threaded at 70 over the rear end of the forward barrel 13. A spring retaining sleeve 71 is assembled over tube 62 and planet carrier 66a and compresses a spring 72 which applies a collet closing force through a spring cup washer 73 and the inner race of bearing 64 to a collet closing sleeve 74. The latter, along with the inner race of bearings 64 is slideable along the collet sleeve 62 and engages over frusto-conical cam surfaces 75 on the collet fingers 64 to close the latter into their illustrated clutching positions. Opening of the collet will be described later.

The drive transmission unit 15 comprises three planetary gears 76, FIGS. 1 and 8, fitted within slots 77 formed in the wall of the carrier 66 and rotatably mounted on pins 78 extending in the carrier. When the forward barrel 13 is located in its forward position shown in FIG. 1, the planetary gears 76 mesh with both the ring gear 17 and a sun gear 80 affixed to the forward trunnion extension 25 of the rotor 24. Accordingly, rotation of the sun gear 80 will cause the planetary gears 76 to revolve about their axes with the stationary ring gear 17, causing the carrier 66 and collet 14 to rotate at a lower speed, the gear ratios being such that the collet 14 will rotate at one quarter the speed of the rotor 24. When the barrel 13 is slid rearward to an intermediate position shown in FIG. 3, in a manner to be described later, the planetary gears 76 are moved endwise out of mesh with the ring gear 17 but will remain in mesh with the sun gear 80. At this time, a forward extension 81 of the forward trunnion extension 25, having a square or splined cross-section, is moved into driving engagement with a square or mating hole 82 formed in the carrier 60 to form a direct high speed drive between the air motor and the collet.

Figure 3:
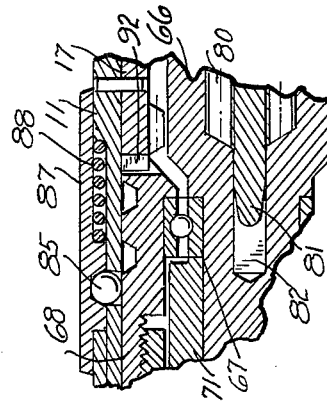
FIG. 3 is a fragmentary longitudinal sectional view through the handpiece, illustrating the same in a high speed or direct drive setting.

For the purpose of enabling swiveling and/or telescoping movement of the forward barrel 13 within the rear barrel 11 and for locking the same in either its forward position of FIG. 1 or its rear position of FIG. 3, the shift ring 68 is provided with two axially spaced circumferential grooves 83 and 84 engageable by balls 85 movable transversely through holes 86 in the wall of barrel 11 and retained in their locking positions in FIGS. 1 and 3 by a locking ring 87. The latter is slideable along the rear barrel 11 and is normally held in its illustrated locking position by a compression spring 88 to hold the balls 85 partly in holes 86 and partly in one of the grooves 83 and 84.

The locking ring 87 is provided with an inner circumferential groove 90, and when the ring is shifted rearward, groove 90 is aligned with the balls 85, permitting the balls 85 to move transversely outward in holes 86, thereby freeing the forward barrel 13 to be shifted from its position shown in FIG. 1 to that shown in FIG. 3 or vice versa where it can again be locked by releasing the locking ring 87 to the action of spring 88.

For the purpose of opening or closing the collet 14, the barrel 13 is screwed into the shift ring 68 a limited amount, causing a counter-bored shoulder 91 in the forward barrel to engage the forward end of the clamping sleeve 74, moving the same rearward against the action of spring 72 to thus allow the collet fingers 64 to spring outwardly.

For the purpose of locking the shift ring 68 against rotation to enable relative rotation of the forward barrel 13 to open or close the collet 14, axially extending teeth 92 are formed on the stationary ring gear 17 which are engageable by similar teeth 93 formed on the shift ring 68. Accordingly, by releasing the locking ring 87 and moving the barrel 13, and thus shift ring 68, to their rearmost positions shown in FIG. 4 relative to the barrel 11, the teeth 92 and 93 interlock, preventing relative rotation, whereupon the barrel 13 may be screwed into the shift ring 68 to release the collet sleeve 74 to open the collet 14 or to unscrew the barrel 13 to permit spring 72 to close the collet.

Figure 5:
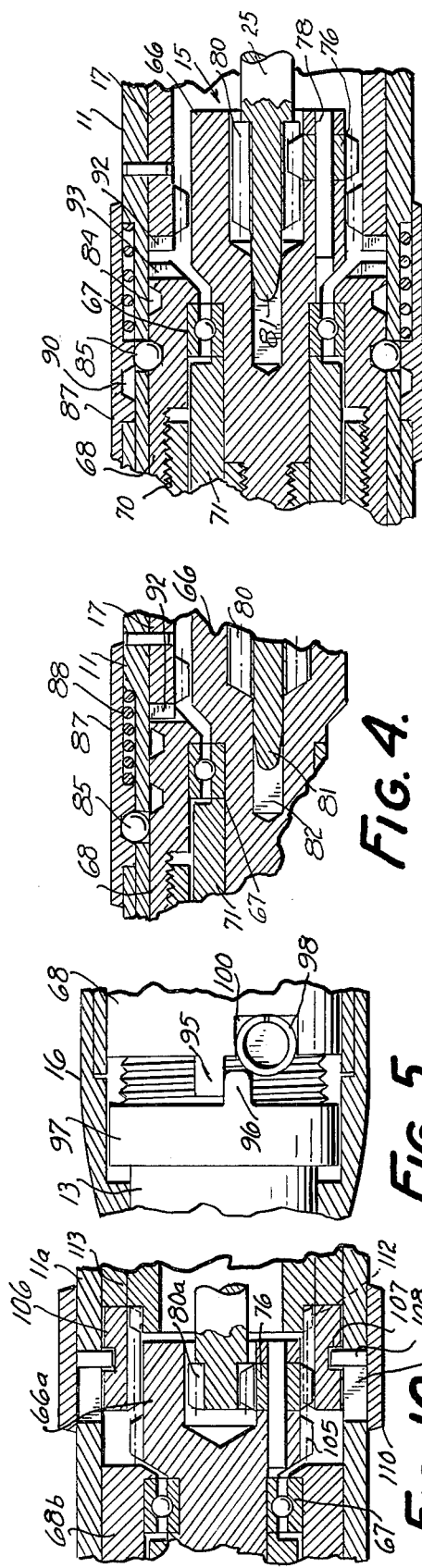
FIG. 5 is a fragmentary longitudinal sectional view, with parts shown in full outline, showing the limit stop arrangement for the forward housing.

Means are provided to limit rotation of the barrel 13 to less than one revolution during collet opening or closing operations. For this purpose, a tooth 95, FIG. 5, is formed in the forward end of the shift ring 68, and is engageable by a tooth 96 formed on the nut 97 threaded on the barrel 13 and secured in position by a suitable adhesive. In order to detent the barrel 13 in its illustrated collet closing position, a circular wire detent spring 98 is fitted in a notch 100 in the shift ring 68 and yieldably engages the tooth 96 when the barrel is rotated to its illustrated collet closing position.

A plug 120 is secured within the collet tube 62 by a suitable adhesive to limit the depth to which a dental burr or other tool can be inserted in the collet 14. The plug has a stepped formation 121 at its forward end which may be engaged by a suitable mating tool for the purpose of threading the collet tube onto the planetary carrier 66.

An important feature of the construction described above is that when the handpiece is in either its high speed setting depicted in FIG. 3 or its low speed setting depicted in FIG. 1, the rear barrel 11 may freely swivel any amount relative to the forward barrel. Normally, the handpiece is held by gripping the forward barrel 13 only so that any torsional forces resulting from twisting or bending of the flexible conduits 48 and 53 will merely cause swiveling of the rear barrel 11 and will therefore not interfere with or influence manipulation of the handpiece.

DESCRIPTION OF ALTERNATE EMBODIMENT SHOWN IN FIG. 9

FIG. 9 illustrates an alternate embodiment for temporarily locking shift ring 68 from rotation relative to barrel 11 to enable opening or closing of the collet. Those parts which are similar to the parts shown in FIGS. 1 to 8 are identified by the same reference numerals.

Figure 4:
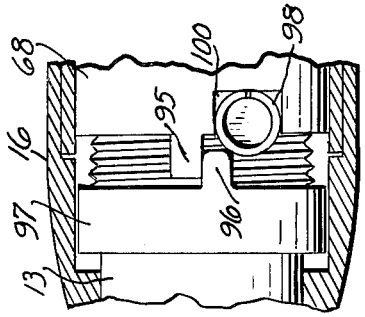
FIG. 4 is a fragmentary longitudinal sectional view similar to FIG. 3, but illustrating the handpiece in a locked setting for opening or closing the collet.

In this construction, the interlocking teeth 92 and 93 of FIGS. 1, 3 and 4 are omitted and, in their place, a locking button 101 is provided, being mounted on a leaf spring 102 fitted and retained in a recess 103 formed in the barrel nosepiece 16a or on the outside of barrel 11. The button 101 extends outwardly through a hole in the wall of the barrel nosepiece 16a and has an inwardly extending locking projection 104. Upon depression of the button 101 and rotating the barrel 13, the locking projection 104 will find and engage in one of a series of notches 107 formed in the shift ring 68a to lock the same against rotation so that the barrel 13 may be screwed into the shift ring 68a a small distance for the purpose of compressing the spring 72 to open the collet 14. Closing of the collet 14 is effected by unscrewing the barrel 13.

DESCRIPTION OF ALTERNATE EMBODIMENT SHOWN IN FIG. 10

Figure 10:
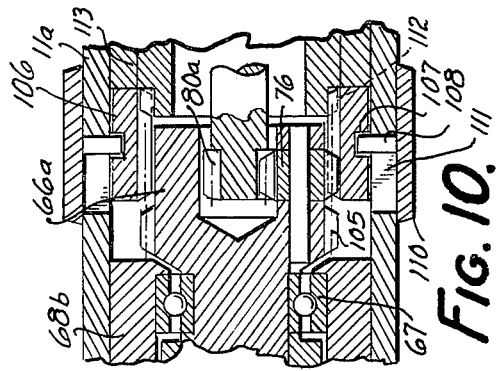
FIG. 10 is a fragmentary longitudinal sectional view illustrating an alternate form of planetary gear drive system.

FIG. 10 illustrates an alternate form of drive transmission unit. In this case, the forward barrel, including ring member 68b, similar to shift ring 68 of FIG. 1, is not shiftable endwise relative to the rear barrel 11a and therefore the locking arrangement including locking sleeve 87 and balls 85 are omitted. Sun gear 80a carried by the rotor meshes with planetary gears 76 carried by the planetary gear carrier 66a. Carrier 66a has an external gear or spline 105 integral therewith. A ring gear 106 is free to slide and/or rotate within the rear barrel 11a and meshes with the planetary gears 76. A circumferential groove 107 formed in the ring gear 106 is engaged by pins 108 carried by a shift ring 110 slideable lengthwise along barrel 11a, the pins 108 being movable through elongated slots 111 in the barrel.

When the ring gear 106 is located in its position shown in FIG. 10, it engages and is locked by teeth 112 formed on a sleeve 113 suitably secured within the barrel 11a. Accordingly, rotation of the sun gear 80a will cause the planetary gears 76, to revolve in mesh with the now locked or stationary ring gear 106, causing the planetary carrier 66a, and therefore the collet, to rotate at a reduced speed relative to the sun gear 80a. However, when the ring gear 106 is shifted forwardly it moves out of locking relation with the teeth 112 and into locking engagement with the teeth 105 on carrier 66a. Now, since the planetary gears 76 are locked against rotation relative to the carrier 66a, the sun gear 80a will transmit a direct drive to the collet at a relatively high speed.

For the purpose of detenting the ring gear 106 in either of its two endwise shifted positions, it is permanently magnetized and polarized axially. The ring 68b and sleeve 113 are formed of ferrous magnetic material. Accordingly, when the ring gear 106 is shifted rearwardly by means of shift ring 110 into its illustrated position, it will be magnetically detented by sleeve 113 and when it is moved forwardly, it will be magnetically detented by the ring 68b.

Alternatively, the shift ring 110 may be mechanically detented in either the forward or aft position by suitable spring detents, not shown, and additionally can provide axial support and location for a throwout bearing which positions the floating ring gear 106 axially relative to the shift ring 110 while allowing it to rotate freely in the direct drive mode or holding the ring gear fixed against the sleeve 113 in the 4 to 1 speed reducing mode.

I claim:
1. A dental handpiece comprising
a first housing barrel,
a second housing barrel manually slideable in said first barrel,
said second barrel being slideable from a first position to a second position,
means for selectively locking said second barrel in either of said positions,
a motor carried by one of said barrels,
a rotary chuck rotatable in the other of said barrels,
a variable speed transmission mechanism intermediate said motor and said chuck,
means responsive to movement of said second barrel to said first position to adjust said transmission mechanism to transmit rotation to said chuck at one ratio and responsive to movement of said second barrel to said second position to adjust said transmission mechanism to transmit rotation to said chuck at a different ratio.

2. A dental handpiece as defined in claim 1 wherein said last mentioned means is responsive to movement of said second barrel to said second position to adjust said transmission mechanism to directly connect said motor to said chuck.

3. A dental handpiece as defined in claim 1 wherein said second barrel is slideable endwise in said first barrel from one of said positions thereof to the other.

4. A dental handpiece as defined in claim 3 wherein one of said barrels is adapted to freely relative to the other in either of said two positions of said second barrel.

5. A dental handpiece as defined in claim 1
wherein said locking means comprises a sleeve member manually movable lengthwise relative to said barrels to a first location to lock said second barrel in either of said positions thereof and movable to a second location to enable movement of said second barrel between said positions thereof.

6. A dental handpiece comprising
a first housing barrel,
a second housing barrel movable in said first barrel from a first position to a second position,
a motor carried by one of said barrels,
a rotary chuck carried by the other of said barrels,
a variable speed transmission mechanism intermediate said motor and said chuck,
said transmission mechanism comprising
a drive element operatively connected to said motor,
a driven element operatively connected to said chuck,
a sun gear carried by one of said elements,
a planetary gear carrier carried by the other of said elements,
a planetary gear carried by said carrier and meshing with said sun gear, and
a ring gear carried by said first barrel,
said second barrel being effective upon movement to said first position thereof to mesh said planetary gear with said ring gear and effective upon movement to said second position thereof to couple said drive element to said driven element and to demesh said planetary gear from said ring gear.

7. A dental handpiece comprising a rotatable chuck,
a motor,
a drive element operatively connected to said motor,
a driven element operatively connected to said chuck,
a sun gear carried by one of said elements,
a planetary gear carrier carried by the other said elements,
a planetary gear rotatably carried by said carrier and meshing with said sun gear, and
a stationary ring gear,
one of said elements being shiftable endwise relative to the other of said elements to a first position to mesh said planetary gear with said ring gear and being shiftable endwise to a second position to couple said elements together and to demesh said planetary gear from said ring gear.

8. A dental handpiece comprising a rotatable chuck,
a motor,
a drive element operatively connected to said motor,
a driven element operatively connected to said chuck,
a sun gear carried by one of said elements,
a planetary gear carrier carried by the other said elements for rotation about an axis concentric with the axis of said sun gear,
a planetary gear rotatably carried by said carrier and meshing with said sun gear,
a ring gear meshing with said planetary gear,
a fourth gear carried by said carrier concentrically of said sun gear, and
means for locking said ring gear from rotation, said ring gear being movable endwise to a first position to engage said locking means and to demesh from said fourth gear and movable endwise to a second position to mesh with said fourth gear and to disengage from said locking means.

9. A dental handpiece as defined in claim 8 comprising means for detenting said ring gear in each of said positions thereof.

* * * * *